United States Patent [19]

Boettcher et al.

[11] Patent Number: 4,539,206

[45] Date of Patent: Sep. 3, 1985

[54] TOPICAL COMPOSITIONS CONTAINING COPPER (II) COMPLEXES OF 3,5-DIOXO-PYRAZOLIDINE DERIVATIVES AND METHODS OF COMBATTING INFLAMMATION WITH THEM

[75] Inventors: Barry Boettcher, New Lambton; William R. Walker, Merewether, both of Australia

[73] Assignee: Alcusal Incorporated Pty. Ltd., New South Wales, Australia

[21] Appl. No.: 375,047

[22] Filed: May 5, 1982

[30] Foreign Application Priority Data

May 6, 1981 [AU] Australia ............................. PE8726

[51] Int. Cl.$^3$ .................. A61K 31/30; A61K 31/415; C07F 1/08
[52] U.S. Cl. .................................... 514/184; 548/101; 548/105
[58] Field of Search ............... 548/101, 103, 107, 105; 424/245

[56] References Cited

U.S. PATENT DOCUMENTS

| | | | |
|---|---|---|---|
| 3,389,050 | 6/1968 | Dulin et al. | 424/245 |
| 4,008,200 | 2/1977 | Avar et al. | 548/105 X |
| 4,053,621 | 10/1977 | Möller et al. | 424/273 P |
| 4,207,317 | 6/1980 | Walker | 424/245 |
| 4,221,785 | 9/1980 | Sorenson | 424/130 |

OTHER PUBLICATIONS

Sorenson, J. Med. Chem., vol. 19, No. 1, pp. 135–148 (1976).

*Primary Examiner*—Donald G. Daus
*Assistant Examiner*—Diana G. Rivers
*Attorney, Agent, or Firm*—Ostrolenk, Faber, Gerb & Soffen

[57] ABSTRACT

Novel copper (II) coordination complexes of 3,5-dioxo-pyrazolidine derivatives with dimethylsulphoxide, dimethylformamide, and 1,4-dioxan coordination ligands are described. The complexes are potent anti-inflammatory agents and are usually applied topically in non-aqueous solution, showing good dermal penetration and systemic absorption.

8 Claims, 3 Drawing Figures

Figure 1:
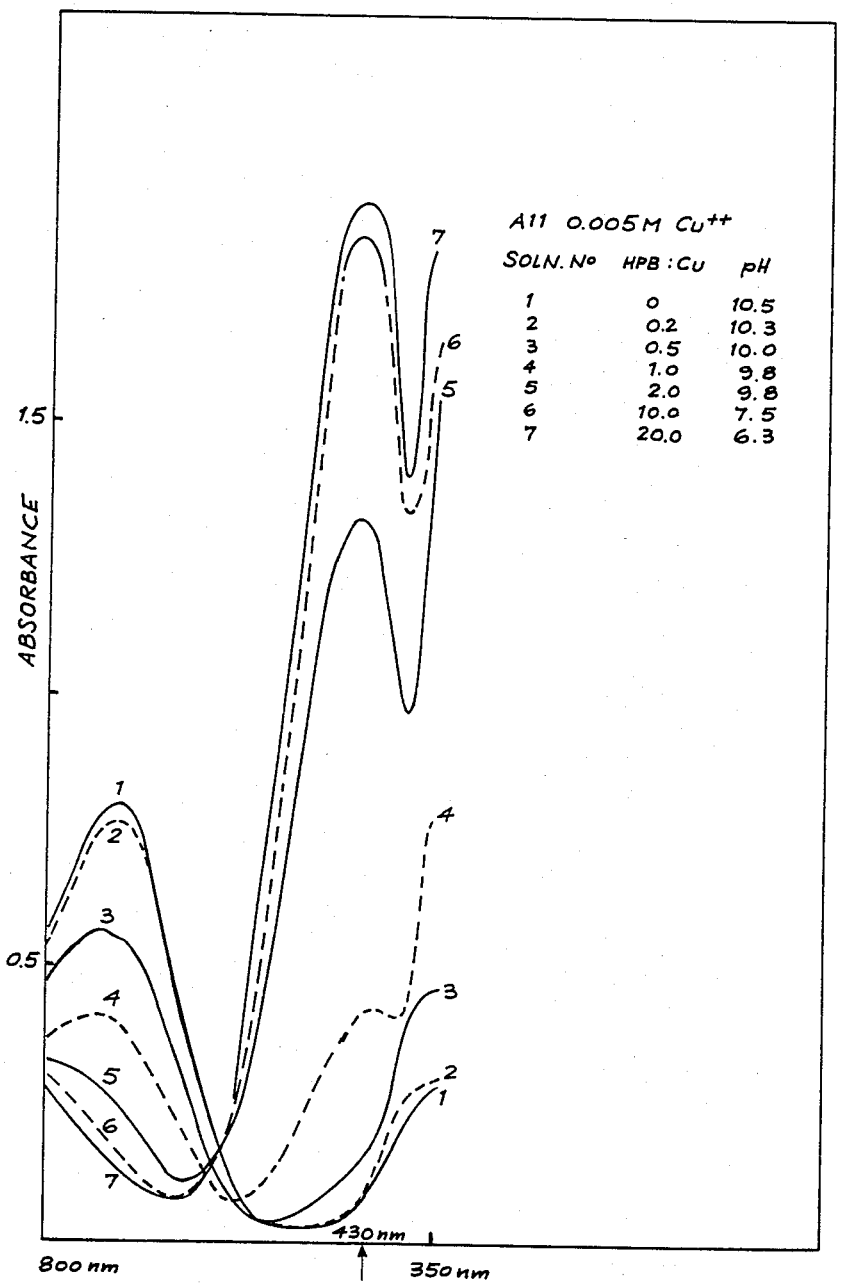

FIG. 1 SPECTRA of COPPER ACETATE with PHENYLBUTAZONE (HPB) in D.M.S.O.

SPECTRAL DATA of COPPER-PHENYLBUTAZONE in D.M.S.O.

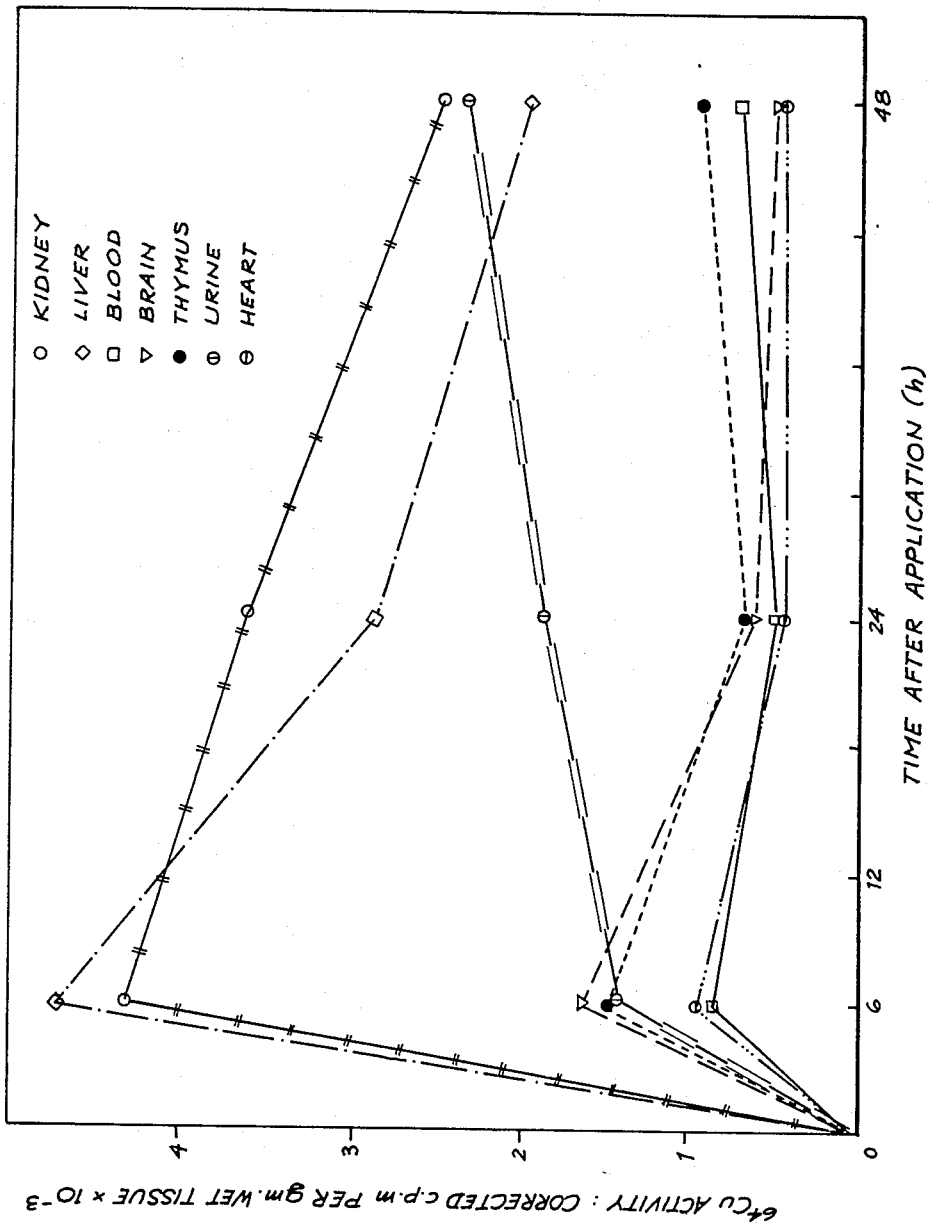

TOPICAL COMPOSITIONS CONTAINING COPPER (II) COMPLEXES OF 3,5-DIOXO-PYRAZOLIDINE DERIVATIVES AND METHODS OF COMBATTING INFLAMMATION WITH THEM

The present invention relates to copper (II) complexes of 3,5-dioxo-pyrazolidine derivatives, pharmaceutical compositions containing the complexes, methods of preparation of the complexes and methods of treatment. The complexes have an anti-inflammatory and anti-arthritic activity.

The copper complexes of the invention may be represented by formula (I)

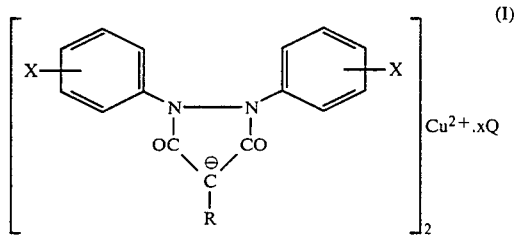

wherein
X is H, OH, halo, or $C_1$–$C_{10}$ alkyl,
R is H or $C_1$–$C_{10}$ alkyl,
Q is a ligand selected from dimethylsulphoxide, dimethylformamide and 1,4-dioxan, and
x is 1, 2, 3 or 4.
Preferably, X is selected from Br or Cl.

The preferred compounds of the invention are the copper (II) di(phenylbutazone) complexes, wherein R is butyl and X is hydrogen, which exhibit good activity.

In the complexes, the copper is in the divalent state. The negatively charged heterocyclic moiety may exist in a number of tautomeric forms, including the enol tautomers.

The invention also relates to a method of preparation of a copper complex which comprises reacting Cu(II) in a non-aqueous solution containing dimethylsulphoxide, dimethylformamide or 1,4-dioxan with a compound of formula (II)

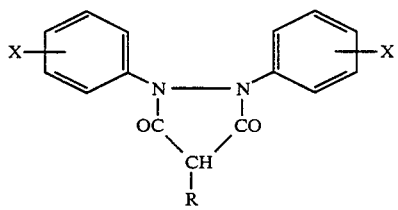

wherein X and R have the meanings given above.

The copper compound may be a salt, such as copper (II) acetate, or may be copper (II) hydroxide.

In solution, an equilibrium mixture of reactants and product is generally formed. For example, the equilibrium constant K for the Cu(PB)$_2$. xDMSO complex is approximately log K=4.7. Hereafter PB will be used to denote dihydrophenylbutazone radical and HPB to denote phenylbutazone itself. DMSO and DMF will be used as abbreviations for dimethylsulphoxide and dimethylformamide respectively.

Up to the present time, it has not been possible to isolate the complexes from solution. In an effort to investigate the conditions necessary to prepare the copper complexes of the present invention, the following preparations of the copper phenylbutazone-DMSO complex under non-aqueous conditions were attempted.

(1) Anhydrous CuCl$_2$ (1 g) was dissolved in hot ethanol (10 ml). When phenylbutazone (2.3 g) dissolved in boiling ethanol (40 ml) was added, a copious white precipitate formed. This appeared to be unreacted phenylbutazone.

(2) When Cu(OH)$_2$ (0.33 g) and phenylbutazone (2g) were dry-mixed and placed in DMSO (30 ml), the mixture slowly dissolved forming a deep-brown solution of the complex Cu(PB)$_2$.xDMSO. This had an identical I.R. spectrum to that solution prepared from copper (II) acetate and phenylbutazone in DMSO described below at (4).

(3) When benzene was used instead of DMSO as solvent in a procedure similar to (2) above, no reaction occurred.

(4) When a saturated solution of copper (II) acetate and phenylbutazone (HPB) in DMSO in the molar ratio of 1:2 was allowed to stand for four weeks, a brown solution of Cu(PB)$_2$.xDMSO resulted, but no crystals appeared. When this solution was cooled in an ice-salt bath, the DMSO froze and came out of solution. No other crystals (or solid), however, were obtained.

Figure 2:
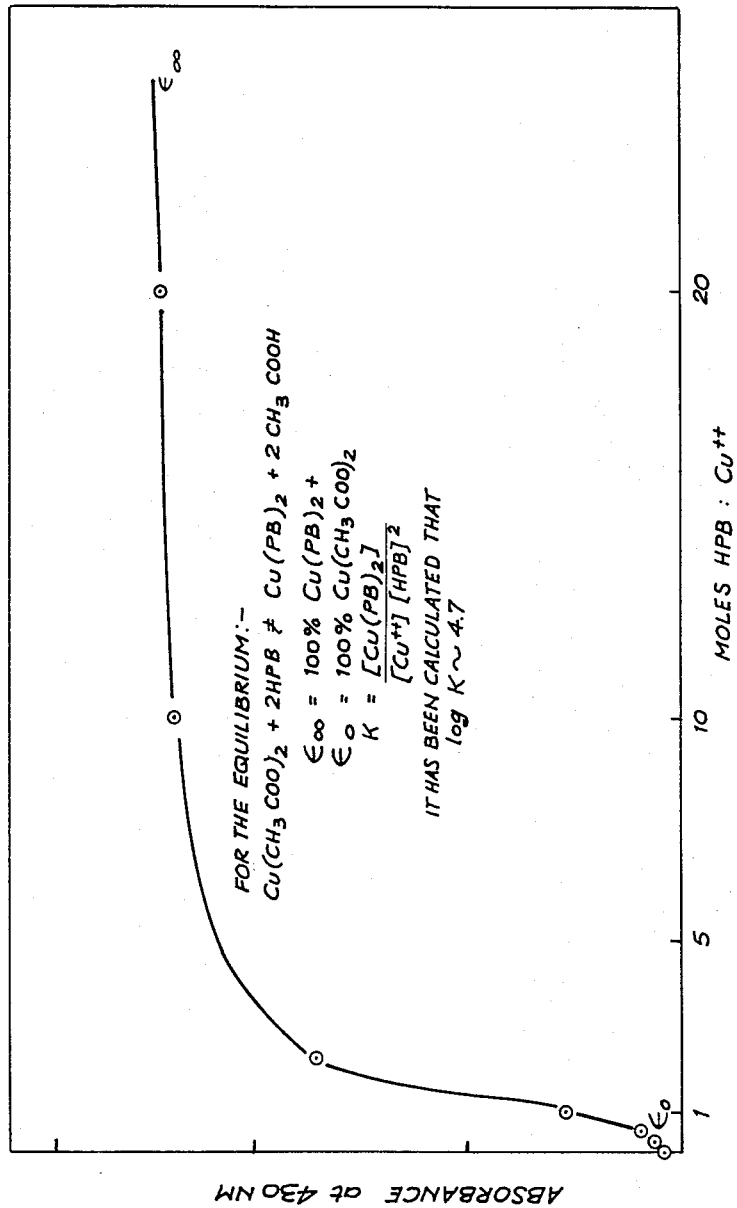

The structure of Cu(PB)$_2$.xDMSO is discussed later in more detail with reference to FIGS. 1 and 2 of the drawings.

The prior art (J. R. Sorenson, J. Med. Chem. 19 (1976) 147) describes a copper phenylbutazone complex prepared in aqueous solution and reported to have the formula Cu$_2$(PB)$_4$. However, the green solid prepared by Sorenson clearly represents a different complex from the deep brown copper phenylbutazone complex prepared according to the present invention.

The present applicants have ascertained that dissolving the green solid prepared according to the method of Sorenson in DMSO leads to the formation of a deep brown solution of the Cu(PB)$_2$.xDMSO complex of the present invention. The colour change is evidence of the formation of a DMSO coordination complex.

The copper complexes of the invention have been found to be particularly useful in the treatment of inflammatory diseases in humans and animals. Thus, in a further embodiment of the invention there is provided a method of treatment of inflammatory diseases in animals or humans which comprises administering an effective amount of the copper complex. The complexes are effective against gout, arthritis and so-called gouty arthritis.

A further aspect of the invention provides an anti-inflammatory composition for topical application which comprises a compound of formula (III)

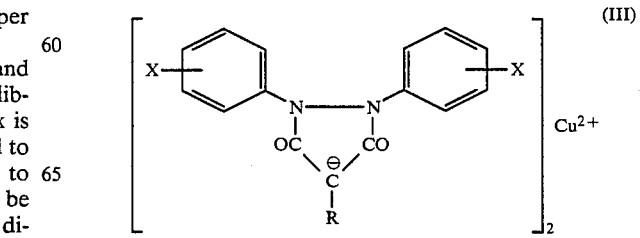

wherein
X is H, OH, halo or $C_1$–$C_{10}$ alkyl and
R is H or $C_1$–$C_{10}$ alkyl
dissolved in a pharmaceutically acceptable non-aqueous lipophilic solvent enabling dermal penetration.

The pharmaceutical composition may also comprise an admixture of the copper complex and a pharmaceutically acceptable non-aqueous solvent. Generally, the composition is formulated for topical application in a lipophilic solvent enabling dermal penetration. Preferred solvents include dimethylsulphoxide, dimethylformamide, 1,4-dioxan; monohydric, dihydric or polyhydric alcohols; and mixtures thereof. The alcohol may be ethanol, isopropyl alcohol, ethylene glycol, propylene glycol or glycerol. Good results in terms of dermal penetration are achieved with solvents comprising DMSO. A solvent comprising 20–80 wt % DMSO and 80–20 wt % glycerol is particularly preferred. The composition may comprise the equilibrium reaction mixture formed as the product of the method of preparation.

The composition for topical application may be in the form of a gel, ointment, paste, cream or lotion. Buffers may be provided to maintain a substantially neutral pH and thereby avoid irritation to the skin. An emollient may also be included.

Typically, a 0.05 to 0.20 M solution of the complex is applied, generally at an application rate of from 1 to 20 ml per kilogram body weight.

The invention will now be further illustrated with reference to the following Examples.

EXAMPLE 1

(Preparation)

A copper phenylbutazone complex was prepared by dissolving copper (II) acetate monohydrate (9.9 g) and phenylbutazone (38.6 g) in hot DMSO (400 ml) to yield a deepbrown solution of the complex $Cu(PB)_2$.

DMF and 1,4-dioxan coordination complexes are prepared in analogous manner.

EXAMPLE 2

(Preparation)

When $Cu(OH)_2$ (0.33 g) and phenylbutazone (2 g) were drymixed and placed in DMSO (30 ml), the mixture slowly dissolved forming a deep-brown solution of the complex $Cu(PB)_2$. This had an identical infrared spectrum to the DMSO solution prepared in Example 1.

EXAMPLE 3

(Composition For Topical Application)

A composition for topical application was prepared by adding glycerol (100 ml) to the cooled deep-brown solution obtained in Example 1.

The composition was tested informally by a veterinarian, who reported that the composition showed excellent results in the treatment of chronic inflammatory lesions. Tests were also carried out on horses by race horse trainers who reported that the composition was effective in musculoskeletal inflammatory conditions.

Phenylbutazone is at present commonly administered orally at a dose of 100–200 mg/day to humans but may lead to the following side effects: oedema, nausea, rash formation, reactivation of a latent peptic ulcer and agranulocytosis. However, when the above composition of $Cu(PB)_2$ in DMSO/glycerol is applied topically, 1–2 ml per day will deliver 70–140 mg of phenylbutazone into the patient's system, alleviating such side effects.

EXAMPLE 4

(Spectral Studies)

The following solutions were prepared in DMSO using stock solutions of 0.01 M copper (II) acetate (A) and 0.20 M phenylbutazone (B)

| solution no. | A (ml) | B (ml) | DMSO (ml) | pH |
| --- | --- | --- | --- | --- |
| 1 | 10 | 0 | 10 | 10.5 |
| 2 | " | 0.1 | 9.9 | 10.3 |
| 3 | " | 0.25 | 9.75 | 10.0 |
| 4 | " | 0.5 | 9.5 | 9.8 |
| 5 | " | 1.0 | 9.0 | 9.8 |
| 6 | " | 5.0 | 5.0 | 7.5 |
| 7 | " | 10.0 | 0 | 6.3 | and the spectra were measured using a Varian Techtron 634S UV-visible spectrophotometer and 1 cm cells.

The spectra from 800–350 nm are shown in FIG. 1. In FIG. 2, a plot of absorbance (arbitrary scale) at 430 nm versus molar ratio of phenylbutazone (HPB) to copper has been made. From this, room temperature equilibrium constants have been eliminated. For the reaction:

$$Cu^{2+} + 2HPB \rightleftharpoons [Cu(PB)_2] + 2H^+$$

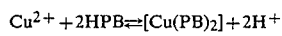

$$\log K \sim 4.7$$

These data afford srong chemical evidence for the formation of a bis-complex of phenylbutazone and copper. The pHs of the solutions have been measured and are listed above and in FIG. 1. They decrease from 10.5 to 6.3. This supports the above equilibrium, which predicts that increased phenylbutazone concentration will move the equilibrium position to the right and produce an increased hydrogen ion concentration (i.e. a reduced pH).

EXAMPLE 5

(Biological Assays)

We have carried out assays for acute anti-inflammatory and anti-arthritic activities by procedures described previously in W. R. Walker, S. J. Beveridge and M. W. Whitehouse, "Anti-inflammatory Activity of a Dermally Applied Copper Salicylate Preparation (Alcusal)", Agents and Actions 10, 38 (1980).

(a) Male Wistar rats were shaved (ca 20 cm²) behind the neck and a solution of 0.1 M copper (II) acetate containing 0.25 M phenylbutazone in DMSO was applied (5 ml/kg). The first application was made 2.5 hr before injecting sodium carrageenan solution into the paw (a 0.1 ml injection delivering 1 mg in 0.15 M NaCl) to induce oedema. A second application of the copper phnylbutazone, if made, was at 1.5 hr before the carrageenan was injected.

The swelling was measured unidimensionally as increase in paw thickness after 2 and 4 hrs using a micrometer screw gauge. Controls were treated with DMSO only. The results were as follows:

| number of times applied | suppression of paw oedema % inhibition of paw swelling | |
| --- | --- | --- |
| | at 2 hr | at 4 hr |
| ×1 | 34% | 33% |

-continued

| number of times applied | suppression of paw oedema % inhibition of paw swelling | |
|---|---|---|
| | at 2 hr | at 4 hr |
| ×2 | 65% | 71% |

(b) A commercial preparation of hydroxylapatite (Calbiochem) was ground in a mortar and then suspended in 0.15 M NaCl (50 mg/ml) for use as an alternative oedemagen to sodium carrageenan. After injecting 0.15 ml of this suspension, paw thickness was measured at 2 and 4 hr later. The [Cu(PB)$_2$].x DMSO solution was as described above. The results were as follows:

| number of times applied | % inhibition of paw swelling | |
|---|---|---|
| | at 2 hr | at 4 hr |
| ×2 | 42% | 76% |

(c) The same [Cu(PB)$_2$] solution was applied once daily (5 ml/kg) for 4 days to arthritic PVG x DA rats beginning on 12th day after inoculating an arthritogenic adjuvant (500 μg *M. tuberculosis* in 50 μl squalane) into the tail base. All animals were selected for measurable signs of *established* arthritis by day 12.

The controls were treated with DMSO only. The results were as follows:

| | increase in paw thickness (mm)* | | change in fore paws** |
|---|---|---|---|
| | rear paws | tail | |
| Controls (DMSO) | 2.2 ± 0.1 | 0.9 ± 0.2 | 4+ |
| [Cu(PB)$_2$].x(DMSO) | 0.4 ± 0.1 | 0.3 ± 0.2 | 2+ |
| HPB (DMSO) | 1.0 ± 0.2 | 0.3 ± 0.1 | 3+ |

*Difference between measurements made on day 12 and on day 16; values are means ± standard error.
**Mean increase in arthritic signs of both forepaws/animal; signs and swelling were scored on scale of 0 to 4+ on days 12 and 16.

EXAMPLE 6

(Bio-distribution of $^{64}$Cu(PB)$_2$.x DMSO)

(1) The copper (II) phenylbutazone complex labelled with $^{64}$Cu was prepared as follows: Radioactive copper (II) acetate containing 3 mCi of $^{64}$Cu (A.A.E.C. Lucas Heights) was mixed with copper (II) acetate monohydrate (0.250 g), phenylbutazone (0.964 g) and dissolved in DMSO (10 ml). Glycerol (2.5 ml) was added later. This stock solution had an activity in excess of $11.3 \times 10^6$ cpm ml$^{-1}$.

(2) Topical Application to Rats

Six male white rats (average weight 250 g) were anaesthetised with halothane and an area of skin (ca 20 cm$^2$) immediately below the neck was shaved with electric hair clippers. Two aliquots (each 0.75 ml) were applied to each rat, whilst anaesthetised, over a period of one hour.

Each rat was placed separately in an experimental cage which permitted collection of both urine and faeces. At times of 6, 24 and 48 hours after topical application, two rats were anaesthetised with ether and euthenased by decapitation in a guillotine. Blood was collected and the organs listed in FIG. 3 were dissected out. Each organ except the thymus, spleen and the adrenals were cut into two samples for more accurate counting. This was done on a Packard automatic γ spectrometer for periods from 1 to 10 minutes.

All counts were corrected to zero time per gram of wet tissue. After 24 and 48 hours, the faeces were dry and the activity in them is not recorded in FIG. 3.

In Table 1, the results for the location in the rats of the $^{64}$Cu activity at 6, 24 and 48 hours after topical application are shown. These data are based on actual organ weights and an assumption of total blood volume and urine and faecal output.

TABLE 1

Bio-distribution of $^{64}$Cu as % of Original Applied

| Location | Time (h) | | |
|---|---|---|---|
| | 6 | 24 | 48 |
| Kidney | 0.04 | 0.04 | 0.04 |
| Liver | 6.22 | 0.17 | 0.15 |
| Blood (20 ml) | 0.09 | 0.08 | 0.08 |
| Brain | 0.02 | 0.01 | 0.01 |
| Thymus | 0.01 | —* | — |
| Adrenals | — | — | — |
| Urine | 0.04 | 0.21 | 0.40 |
| Faeces | 0.07 | 28.9 | 49.9 |
| Skin (application site) | 5.34 | 3.81 | 1.02 |
| Heart | 0.01 | — | — |
| Spleen | 0.01 | — | 0.01 |

* = less than 0.004%

The data of FIG. 3 and Table 1 clearly show that the copper (II) complex of phenylbutazone, after topical application, readily enters the bloom stream. The $^{64}$Cu is cleared from the system in several days, about 50% being found in the faeces after two days. The activity of the $^{64}$Cu in the skin at the site of application decreases linearly with time and is typical of other percutaneous absorption studies.

Thus, it is clear that there is excellent dermal penetration of the copper (II) phenylbutazone-DMSO complex.

We claim:

1. An anti-inflammatory composition for topical application which comprises a compound of formula (III)

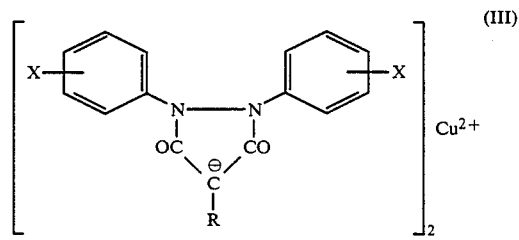

wherein
X is H, OH, halo or C$_1$–C$_{10}$ alkyl and
R is H or C$_1$–C$_{10}$ alkyl
dissolved in a pharmaceutically acceptable non-aqueous lipophilic solvent enabling dermal penetration.

2. A composition according to claim 1 wherein the solvent comprises dimethylsulphoxide, dimethylformamide, 1,4-dioxan; monohydric, dihydric or polyhydric alcohols; or mixtures thereof.

3. A composition according to claim 1 wherein the solvent is dimethylsulphoxide.

4. A composition according to claim 2 wherein the solvent comprises 20–80 wt % dimethylsulphoxide and 80–20 wt % glycerol.

5. A method of combatting inflammation which comprises topically administering to a human or animal patient a copper complex of the formula (III)

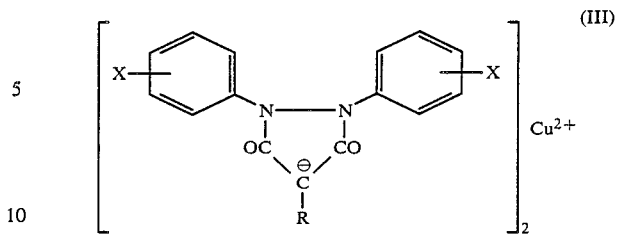

wherein
X is H, OH, halo or $C_1$–$C_{10}$ alkyl and
R is H or $C_1$–$C_{10}$ alkyl
dissolved in a pharmaceutically acceptable non-aqueous lipophilic solvent enabling dermal penetration.

6. A method according to claim 5 wherein the solvent comprises dimethylsulphoxide.

7. A method according to claim 6 wherein the solvent further comprises glycerol.

8. A method according to claim 5 wherein 1 to 20 ml/kg bodyweight of a 0.05 to 0.20 M solution of the copper complex are administered topically per day.

* * * * *